US012758634B2

(12) United States Patent
Dreher et al.

(10) Patent No.: US 12,758,634 B2
(45) Date of Patent: Oct. 13, 2026

(54) TREATMENT OF PROSTATE CANCER

(71) Applicant: Boston Scientific Medical Device Limited, County Galway (IE)

(72) Inventors: Matthew Dreher, Rockville, MD (US); Samdeep Mouli, Chicago, IL (US); Riad Salem, Chicago, IL (US)

(73) Assignees: BOSTON SCIENTIFIC MEDICAL DEVICE LIMITED, Galway (IE); NORTHWESTERN UNIVERSITY, Evanston, IL (US)

( * ) Notice: Subject to any disclaimer, the term of this patent is extended or adjusted under 35 U.S.C. 154(b) by 30 days.

(21) Appl. No.: 18/105,421

(22) Filed: Feb. 3, 2023

(65) Prior Publication Data

US 2023/0248829 A1 Aug. 10, 2023

Related U.S. Application Data

(60) Provisional application No. 63/306,820, filed on Feb. 4, 2022.

(51) Int. Cl.

| | |
|---|---|
| ***A61P 35/00*** | (2006.01) |
| ***A61K 9/00*** | (2006.01) |
| ***A61K 9/16*** | (2006.01) |
| ***A61K 41/00*** | (2020.01) |
| ***A61N 5/10*** | (2006.01) |
| ***A61P 15/00*** | (2006.01) |

(52) U.S. Cl.
CPC ........ *A61K 41/0085* (2013.01); *A61K 9/0034* (2013.01); *A61K 9/16* (2013.01); *A61N 5/1002* (2013.01); *A61N 5/1007* (2013.01); *A61P 15/00* (2018.01); *A61P 35/00* (2018.01); *A61N 2005/1021* (2013.01); *A61N 2005/1089* (2013.01)

(58) Field of Classification Search
CPC ... A61K 41/0085; A61K 9/0034; A61P 15/00; A61N 5/1002
See application file for complete search history.

(56) References Cited

U.S. PATENT DOCUMENTS

| | | | | |
|---|---|---|---|---|
| 7,959,900 | B2 | 6/2011 | Peng et al. | |
| 8,697,030 | B2 | 4/2014 | Peng et al. | |
| 9,119,887 | B2 | 9/2015 | Day et al. | |
| 9,539,347 | B2 | 1/2017 | Day et al. | |
| 9,839,705 | B2 | 12/2017 | Day et al. | |
| 9,849,200 | B2 | 12/2017 | Day et al. | |
| 10,232,062 | B2 | 3/2019 | Stephens et al. | |
| 10,232,063 | B2 | 3/2019 | Ricke et al. | |
| 2010/0016932 | A1* | 1/2010 | Weinberg | A61B 90/04 600/7 |
| 2016/0331854 | A1 | 11/2016 | Fritz | |
| 2018/0265402 | A1* | 9/2018 | Filiaggi | A61K 9/1611 |
| 2020/0289680 | A1* | 9/2020 | Dreher | A61K 9/0019 |

FOREIGN PATENT DOCUMENTS

| | | | |
|---|---|---|---|
| EP | 1615671 | B1 | 5/2014 |
| WO | 2017053398 | A1 | 3/2017 |
| WO | 2018028644 | A1 | 2/2018 |

OTHER PUBLICATIONS

Peter J. Hoskin, et al. High dose rate brachytherapy in combination with external beam radiotherapy in the radical treatment of prostate cancer: initial results of a randomised phase three trial, Radiotherapy and Oncology, vol. 84, Issue 2, 2007, pp. 114-120. (Year: 2007).*
Greene (1963) Embolization of Dog Prostates with Yttrim-90 Microspheres, Journal of Urology (U.S.) vol. 90, pp. 451-457 (Year: 1963).*
Anderson et al., "Production and Properties of Radioactive Microspheres for Localized Irradiation of Lung Tissue," Health Physics, Pergamon Press, vol. 34, pp. 225-236, Printed in Great Britain, 1978.
Ariel et al., "The Treatment of Cancer Metastases in the Lung by Means of Radiating Microspheres," Pack Medical Foundation, Inc. and the Division of Nuclear Medicine, Department of Radiation Therapy, Hospital for Joint Diseases, New York, NY, 22 pages, 1967.
Botta et al., "Investigation of 90Y-Avidin for Prostate Cancer Brachytherapyia Dosimetric Model for a Phase I-II Clinical Study," European Journal of Nuclear Medicine and Molecular Imaging, vol. 40, Issue 7, pp. 1047-1056, Jul. 2013. Accessed Nov. 11, 2021.
BTG "Methods of Treatment-Radioactive Microspheres + Microbubbles + Ultrasound," Powerpoint Presentation 4 slides, 2021.
BTG "Y90 Glioma Summary with a Subtitle," Powerpoint Presentation, 9 slides, 2019.
Greene "Embolization of Dog Prostates with Yttrium-90 Microspheres," Journal of Urology (U.S.) vol. 90, pp. 1-3, Oct. 1, 1963, Accessed Nov. 11, 2021.
Kennedy et al., "Radioembolization (Yttrium-90 Microspheres) for Primary and Metastatic Hepatic Malignancies," The Cancer Journal, vol. 16, No. 21, pp. 163-175, Mar./Apr. 2010.
Mouli et al., "Prostate Artery Embolization," Seminars in Interventional Radiology, vol. 36, pp. 142-148, 2019.
Mouli et al., "Yttrium-90 Radioembolization to the Prostate Gland: Proof of Concept in a Canine Model and Clinical Translation," Journal of Vascular and Interventional Radiology, vol. 32, pp. 1103-1112, 2021.

(Continued)

*Primary Examiner* — Sue X Liu
*Assistant Examiner* — Susannah S Armstrong
(74) *Attorney, Agent, or Firm* — Seager, Tufte & Wickhem, LLP

(57) ABSTRACT

Disclosed herein are methods of treating a patient in need of therapy for prostate cancer comprising delivering a β-radiation-emitting composition into the prostatic vasculature. In some embodiments, an absorbed dose of 60 Gy to 200 Gy is delivered to the prostate. In some embodiments, the β-radiation-emitting composition is delivered into the arterial vasculature of the prostate via a catheter. In some embodiments, the β-radiation-emitting composition comprises a suspension of the β-radiation-emitting particles in an aqueous liquid.

14 Claims, No Drawings

(56) References Cited

OTHER PUBLICATIONS

Lewandowski et al., "Radiation Segmentectomy: Potential Curative Therapy for Early Hepatocellular Carcinoma," Radiology, vol. 287, pp. 1050-1058, 2018.
Simon et al; Intra-Arterial Irradiation of Tumors, a Safe Procedure, Presented at the Seventy-First Meeting of the American Roentgen Ray Society, vol. 112, No. 4, pp. 732-739, Aug. 1971. Accessed Sep. 2, 2020 from www.ajronline.org.
Vince "Using Ultrasound to Enhance Targeted Radiotherapy," DPhil Transfer Report, 50 pages, 2019.
Vince, "Using Ultrasound to Improve Radiation Therapy," Powerpoint Presentation, 18 Slides, Nov. 27, 2019.
Hamdy et al., "Ten Year Outcomes after Monitoring, Surgery, or Radiotherapy for Localized Prostate Cancer," New England Journal of Medicine, vol. 375, pp. 1415-1424, 2016.
Donovan et al., "Patient Reported Outcomes after Monitoring, Surgery or Radiotherapy for Prostate Cancer," New England Journal of Medicine, vol. 375, pp. 1425-1437, 2016.
Mylona et al., "Local Dose Analysis to Predict Acute and Late Urinary Toxicities after Prostate Cancer Radiotherapy: Assessment of cohort and Method Effects," Radiotherapy and Oncology, vol. 147, pp. 40-49, Jun. 2020.
Mylona et al., "Rectal and Urethro-Vesical Subregions for Toxicity Prediction after Prostate Cancer Radiation Therapy: Validation of Voxel-Based Models in an Independent Population," International Journal of Radiation Oncology Biology Physics, vol. 108, pp. 1189-1195, 2020.
Vanstam et al; "Patient-Reported Outcomes Following Treatment of Localized Prostate Cancer and their Association with Regret about Treatment Choices," European Urology Oncology, vol. 3, pp. 21-31, 2020.
Pisco et al., "Randomized Clinical Trial of Prostatic Artery Embolization Versus a Sham Procedure for Benign Prostatic Hyperplasia," European Urology, vol. 77, pp. 354-362, 2020.
Pisco et al,. "Safety and Efficacy of Prostatic Artery Chemoembolization for Prostate Cancer-Intitial Experience," Journal of Vasccular Interventional Radiology, vol. 29, pp. 298-305, 2018.
Litwin et al., "The Diagnosis and Treatment of Prostate Cancer: a Review," Journal of the American Medical Association, vol. 317, pp. 2532-2542, 2017.
Leibovici et al., "Pathological Characteristics of Prostate Cancer Recurrence after Radiation Therapy: Implications for Focal Salvage Therapy," Journal of Urology, vol. 188, pp. 98-102, 2012.
Mordasini et al., "Prostatic Artery Embolization in the Treatment of Localized Prostate Cancer: a Bicentric Prospective Proof-of-Concept Study of 12 Patients," Journal of Vascular and Interventional Radiology, vol. 29, pp. 589-597, 2018.
Pasciak et al; The Number of Microspheres in Y90 Radioembolization Directly Affects Normal Tissue Radiation Exposure,: European Journal of Nuclear Medicine and Molecular Imaging, vol. 47, pp. 816-827, 2020.
Hurwitz et al; "Longitudinal Regret after Treatment for Low and Intermediate Risk Prostate Cancer," Cancer, an International Interdisciplinary Journal of the the American Cancer Society, vol. 123, Issue 21, pp. 4252-4258. Nov. 1, 2017.
Abele et al., "Prostate Perfusion Mapped by Technetium-99m Magroaggrgated Albumin after Selective Arterial Injection," Journal of Vascular and Interventional Radiology, vol. 26, No. 3, pp. 418-425. Mar. 2015.
Brown et al., "Nontarget Radiopaque Embolic Deposition during Prostatic Artery Embolization," Journal of Vascular and Interventional Radiology, vol. 33, Issue 5, pp. 558-563. e1, May 2022.

* cited by examiner

TREATMENT OF PROSTATE CANCER

CROSS-REFERENCE TO RELATED APPLICATION

This application claims the benefit of priority of U.S. Provisional Application No. 63/306,820, filed Feb. 4, 2022, the entire disclosure of which is hereby incorporated by reference herein for all purposes.

FIELD

The present disclosure relates to treatment of prostate cancer using beta-radiation-emitting radionuclides (β-emitting radionuclides) particularly when delivered through the prostatic vasculature.

BACKGROUND

Prostate cancer is the most common noncutaneous cancer in men, with 190,000 cases diagnosed in the United States in 2020 (Litwin M S, Tan H J. The diagnosis and treatment of prostate cancer: a review. JAMA 2017; 317:2532-2542). The usually indolent course of the disease and potential for therapy-related toxicities force patients to make difficult treatment decisions. ProtecT, the first randomized controlled trial comparing surgery and radiotherapy (RT), found no difference in prostate cancer-specific or overall mortality or in metastases between either arm, leaving patients with even more treatment choice uncertainty (Hamdy F C, Donovan J L, Lane J A, et al. Ten-year outcomes after monitoring, surgery, or radiotherapy for localized prostate cancer. N Engl J Med 2016; 375:1415-1424; Donovan J L, Hamdy F C, Lane J A, et al. Patient-reported outcomes after monitoring, surgery, or radiotherapy for prostate cancer. N Engl J Med 2016; 375:1425-1437). Nonoperative candidates are managed with brachytherapy (BT) or external-beam radiotherapy (EBRT). Currently, an estimated 10% of low-risk and 60% of high-risk prostate cancer patients experience biochemical recurrence after curative-intent RT (Leibovici D, Chiong E, Pisters L L, et al. Pathological characteristics of prostate cancer recurrence after radiation therapy: implications for focal salvage therapy. J Urol 2012; 188:98-102). Furthermore, despite improvements in dose delivery and conformity, gastrointestinal (GI) and genitourinary (GU) toxicities persist, ranging from 10% to 30% for both acute and late grade >2 toxicities (Mylona E, Cicchetti A, Rancati T, et al. Local dose analysis to predict acute and late urinary toxicities after prostate cancer radiotherapy: assessment of cohort and method effects. Radiother Oncol 2020; 147:40-49; Mylona E, Ebert M, Kennedy A, et al. Rectal and urethro-vesical subregions for toxicity prediction after prostate cancer radiation therapy: validation of voxel-based models in an independent population. Int J Radiat Oncol Biol Phys 2020; 108:1189-1195). Given these limitations, up to 25% of patients report a treatment related regret following current standard-of-care therapies, demonstrating an unmet clinical need regarding the risk-benefit profile (van Stam M A, Aaronson N K, Bosch J R, et al. Patient-reported outcomes following treatment of localized prostate cancer and their association with regret about treatment choices. Eur Urol Oncol 2020; 3:21-31; Hurwitz L M, Cullen J, Kim D J, et al. Longitudinal regret after treatment for low- and intermediate-risk prostate cancer. Cancer 2017; 123:4252-4258).

Prostate cancer therapy is in need of novel strategies to overcome these risk-benefit limitations. The established safety and efficacy of prostatic artery (PA) embolization for the treatment of lower urinary tract symptoms secondary to benign prostatic hyperplasia (BPH) has opened the door to transarterial prostate cancer interventions (Pisco J M, Bilhim T, Costa N V, et al. Randomized clinical trial of prostatic artery embolization versus a sham procedure for benign prostatic hyperplasia. Eur Urol 2020; 77:354-362). However, both bland and chemoembolization for the treatment of prostate cancer have yielded poor oncologic efficacy results, not reaching equipoise with the current standards of care (Mordasini L, Hechelhammer L, Diener P A, et al. Prostatic artery embolization in the treatment of localized prostate cancer: a bicentric prospective proof-of-concept study of 12 patients. J Vasc Interv Radiol 2018; 29:589-597; Pisco J, Bilhim T, Costa N V, Ribeiro M P, Fernandes L, Oliveira A G. Safety and efficacy of prostatic artery chemoembolization for prostate cancer-initial experience. J Vasc Interv Radiol 2018; 29:298-305).

Intra-arterial delivery β-radiation-emitting compositions, for example, yttrium-90 ($^{90}Y$) containing compositions, have the potential to overcome the limitations of existing strategies by ensuring an improved absorbed-dose distribution, conforming to the intended target, and sparing normal tissue exposure. β-particle emission from β-emitting radionuclides, including $^{90}Y$ radioactive decay, in contrast to other brachytherapies, results in a more localized distribution of the absorbed dose, with 90% of the energy deposited within 5 mm of the microsphere (Pasciak A S, Abiola G, Liddell R P, et al. The number of microspheres in Y90 radioembolization directly affects normal tissue radiation exposure. Eur J Nucl Med Mol Imaging 2020; 47:816-827). $^{90}Y$ radioembolization (RE) for hepatocellular carcinoma has demonstrated the ability to safely deliver high absorbed doses compared with EBRT (Pasciak A S, Abiola G, Liddell R P, et al. The number of microspheres in Y90 radioembolization directly affects normal tissue radiation exposure. Eur J Nucl Med Mol Imaging 2020; 47:816-827; Lewandowski R J, Gabr A, Abouchaleh N, et al. Radiation segmentectomy: potential curative therapy for early hepatocellular carcinoma. Radiology 2018; 287:1050-1058). Although this unique and heterogeneous absorbed-dose localization may spare prostate cancer foci within the prostate, it also provides the opportunity to avoid unwanted radiation in nontarget normal tissues, such as the bladder, rectum, and urethra, providing a novel risk-benefit profile.

SUMMARY

In various aspects, the present disclosure pertains to methods of treating a patient in need of therapy for prostate cancer, which comprise delivering a β-radiation-emitting composition into the prostatic vasculature.

In some embodiments, an absorbed dose of 60 Gy to 200 Gy is delivered to the prostate.

In some embodiments, which can be used in conjunction with the above aspects and embodiments, the β-radiation-emitting composition is delivered into the arterial vasculature of the prostate. For example, the β-radiation-emitting composition may be delivered to one or more left prostatic arteries, one or more right prostatic arteries, or both one or more left prostatic arteries and one or more right prostatic arteries.

In some embodiments, which can be used in conjunction with the above aspects and embodiments, the β-radiation-emitting composition is delivered by injection.

In some embodiments, which can be used in conjunction with the above aspects and embodiments, the β-radiation-emitting composition is delivered through a catheter. For example, the catheter may be a 1.5 Fr to 5 Fr catheter.

In some embodiments, which can be used in conjunction with the above aspects and embodiments, the urethral vasculature of the patient may be constricted while delivering the β-radiation-emitting composition. For example, the urethral vasculature may be constricted by cooling, by pressure, and/or thought the use of one or more pharmacologic agents. In particular embodiments, the urethral vasculature is constricted by cooling the patient's urethra, in which case the urethral vasculature may be constricted by conduction of heat from the urethra to a cooled catheter such as a cooled Foley catheter.

In some embodiments, which can be used in conjunction with the above aspects and embodiments, the β-radiation composition contains one or more radionuclides selected from $^{3}H$, $^{14}C$, $^{32}P$, $^{59}Fe$, $^{47}Ca$, $^{89}Sr$, $^{90}Y$, $^{131}I$, $^{153}Sm$, $^{177}Lu7$, $^{166}Ho$, and $^{169}Er$, typically one or more β-radiation-emitting radionuclides selected from $^{89}Sr$, $^{166}Ho$, $^{153}Sm$, $^{177}Lu$, $^{169}Er$ and $^{90}Y$, more typically, $^{90}Y$ radionuclide.

In some embodiments, which can be used in conjunction with the above aspects and embodiments, the β-radiation-emitting composition comprises β-radiation-emitting particles (e.g., microspheres) that have mean diameter of 5 to 100 μm, typically 10 to 50 μm, more typically 15 to 35 μm, even more typically 20 to 30 μm.

In some embodiments, which can be used in conjunction with the above aspects and embodiments, the β-radiation-emitting composition comprises a suspension of the β-radiation-emitting particles in an aqueous liquid. For example, the β-radiation-emitting composition may comprise a suspension of the β-radiation-emitting particles in sterile, pyrogen-free water, among other aqueous liquids.

In some embodiments, which can be used in conjunction with the above aspects and embodiments, the β-radiation-emitting particles comprise glass particles, polymer particles, or oil particles. In particular embodiments, the β-radiation-emitting particles may comprise insoluble glass microspheres, in which case each milligram of glass may contain between 22,000 and 73,000 microspheres.

In some embodiments, which can be used in conjunction with the above aspects and embodiments, the β-radiation-emitting particles comprise insoluble glass microspheres having yttrium-90 ($^{90}Y$) as an integral constituent of the glass. For example, the β-radiation-emitting particles may comprise aluminosilicate glass particles containing yttrium, more typically glass particles derived from a mixture of 35-45% $Y_2O_3$, 15-25% $Al_2O_3$ and 35-45% $SiO_2$. Typically, at least a proportion of the yttrium in the glass microspheres has been converted to $^{90}Y$ by exposure to radiation.

In some embodiments, which can be used in conjunction with the above aspects and embodiments, the β-radiation-emitting particles have a specific activity ranging from 0.0002 GBq/mg to 0.05 GBq/mg when administered, for example, ranging anywhere from 0.0002 GBq/mg to 0.0004 GBq/mg to 0.001 GBq/mg to 0.002 GBq/mg to 0.004 GBq/mg to 0.01 GBq/mg 0.05 GBq/mg (in other words ranging between any two of the preceding values), typically, a specific activity ranging from 0.0004 to 0.01 GBq/mg when administered.

In some embodiments, which can be used in conjunction with the above aspects and embodiments, the β-radiation-emitting composition comprises β-radiation-emitting microspheres that have a specific activity per microsphere at treatment time of 5000 Bq to 10 Bq, for example, ranging anywhere from 5000 Bq to 2000 Bq to 1000 Bq to 500 Bq to 200 Bq to 100 Bq to 50 Bq to 20 Bq to 10 Bq, typically 2000 Bq to 10 Bq, more typically 1000 Bq to 50 Bq.

In some embodiments, which can be used in conjunction with the above aspects and embodiments, the β-radiation-emitting composition comprises β-radiation-emitting microspheres that result in a number of microspheres per mL of prostate tissue of 1,000 to 40,000, typically 3,000 to 30,000 microspheres per mL of prostate tissue, more typically 5,000 to 20,000 microspheres per mL of prostate tissue.

In some embodiments, which can be used in conjunction with the above aspects and embodiments, the dose delivery is confirmed and used to plan subsequent therapy with post-Y90 PET.

In some embodiments, which can be used in conjunction with the above aspects and embodiments, the prostatic vasculature is embolized to isolate the prostatic arteries.

In some embodiments, which can be used in conjunction with the above aspects and embodiments, the β-radiation-emitting composition is used in combination with externally applied radiation therapy.

Additional aspects and embodiments will become apparent to those skilled in the art upon review of the Detailed Description to follow.

DETAILED DESCRIPTION

As previously noted, the present disclosure relates to treatment of prostate cancer using beta-radiation-emitting radionuclides (β-emitting radionuclides) particularly when delivered through the prostatic vasculature. In various embodiments, the present disclosure relates to the use of injectable compositions comprising radionuclide containing substances in the treatment of prostate cancer.

In some embodiments, the compositions for use in the methods of the present disclosure comprise radionuclide containing substances that are embolic in format, such as β-radiation-emitting particles (e.g., microspheres) that are formed from oil, polymer or glass, β-radiation-emitting compositions may comprise radionuclides selected from $^{3}H$, $^{14}C$, $^{32}P$, $^{59}Fe$, $^{47}Ca$, $^{89}Sr$, $^{90}Y$, $^{131}I$, $^{153}Sm$, $^{177}Lu7$, $^{166}Ho$, and $^{169}Er$. More typical are relatively pure β-emitters, selected from $^{89}Sr$, $^{166}Ho$, $^{153}Sm$, $^{177}Lu$, $^{169}Er$ and $^{90}Y$. Even more typical is $^{90}Y$ radionuclide, which may be in the form, for example, of glass or polymer microspheres. Iodinated $^{131}I$ oils, such as Lipiodol® ethiodized oil may also be employed in some embodiments.

In some embodiments, a non-radioactive nuclide may be administered in a microsphere and delivered to the prostate and then the non-radioactive nuclide activated in situ to cause the nuclide to become a radionuclide. In a typical embodiment, the activation is performed using an electron beam. In a more typical embodiment, the activation is performed by directing the electron beam to the perfused target volume or therapeutic site.

TheraSphere™, available from Boston Scientific Corporation (Marlborough, MA, U.S.A.), consists of insoluble glass microspheres where yttrium-90 ($^{90}Y$) is an integral constituent of the glass. The glass is an aluminosilicate glass containing yttrium, derived from a mixture of 35-45% $Y_2O_3$, 15-25% $Al_2O_3$ and 35-45% $SiO_2$ more specifically it is approximately 40% $Y_2O_3$, approximately 20% $Al_2O_3$ and approximately 40% $SiO_2$. At least a proportion of the yttrium in the glass has been converted to $^{90}Y$ by exposure to radiation.

The mean microsphere diameter ranges from 20 to 30 μm. Each milligram contains between 22,000 and 73,000 microspheres. TheraSphere™ is supplied in 0.6 mL of sterile, pyrogen-free water contained in a 1.0 mL vee-bottom vial secured within a clear acrylic vial shield. TheraSphere™ is available in six dose sizes (i.e., six activities): 3 GBq (81 mCi), 5 GBq (135 mCi), 7 GBq (189 mCi), 10 GBq (270 mCi), 15 GBq (405 mCi) and 20 GBq (540 mCi). Custom dose sizes are also available. Dose sizes for use in the present disclosure (for each side of the prostate), are typically smaller, ranging from 0.3 GBq to 4 GBq, for example, ranging anywhere from 0.3 GBq to 0.5 GBq to 1 GBq to 1.5 GBq to 2 GBq to 4 GBq, typically ranging from 0.3 GBq to 1.5 GBq per side for a 30 g prostate.

TheraSphere™ has a twelve-day shelf life. In one embodiment, reference is made to the specific activity of the composition at calibration. In one embodiment, the day of calibration is referred to as day zero, days one to seven following the calibration day are referred to as the first week, and days eight through twelve are referred to as the second week. In one embodiment, calibration refers to day zero at time zero. In one embodiment, time zero on day zero is noon, United States Eastern Standard Time. TheraSphere™ is indicated for use as selective internal radiation therapy (SIRT) for local tumor control of solitary tumors (1-8 cm in diameter), in patients with unresectable hepatocellular carcinoma (HCC), Child-Pugh Score A cirrhosis, well-compensated liver function, no macrovascular invasion, and good performance status.

A preassembled single use TheraSphere™ Administration Set is provided for each dose. The TheraSphere™ Administration Accessory Kit is supplied to new user sites. The kit includes re-usable accessories including an acrylic box base, top shield, removable side shield, bag hook and a RADOS RAD-60R™ radiation dosimeter (or equivalent).

The yttrium-90, a pure β-emitter, decays to stable zirconium-90 with a physical half-life of 64.1 hours (2.67 days). The average energy of the β-emissions from yttrium-90 is 0.9367 MeV. Following embolization of the yttrium-90 glass microspheres in tumorous tissue, the β-radiation that is emitted provides a therapeutic effect. As with other radionuclide containing materials for use in the methods of the present disclosure, once TheraSphere™ has been administered, it loses its radioactivity in time and cannot be reused.

In various embodiments, the β-radiation-emitting compositions are delivered into the prostate, through a catheter placed into the arteries that supply blood to the prostate. Assuming proper artery selection, the microspheres, being unable to pass through the vasculature of due to arteriolar blockade, are trapped in the prostate and exert a local radiotherapeutic effect.

Other β-radiation-emitting substances include Sir-Spheres™, which are ion exchange resin beads bearing $^{90}$Y radionuclide. These beads have diameter of 20-60 μm and are available from Sirtex Medical Inc. (Woburn, MA. U.S.A.). In one embodiment, the Sir-Spheres™ are modified to increase their specific activity in order to increase the therapeutic effect exerted during their use, which increase in specific activity may be accomplished by increasing the loading of $^{90}$Y into the resin.

A further β-radiation-emitting substance is $^{131}$I iodinated Lipiodol®, the use of which is described by the European Association for Nuclear Medicine monograph and Lipiodol® is available from Guerbet LLC (Princeton, NJ, U.S.A.).

In various aspects, the methods of the present disclosure comprise the administration of β-radiation-emitting substances selectively to the vasculature of a prostate of a patent who has been diagnosed with prostate cancer. In particular embodiments, the methods comprising administering an injectable pharmaceutical composition comprising β-radiation-emitting particles, which are, for example, may be liquid particles (e.g., oil), polymer particles or glass particles, in an aqueous carrier, such as saline or sterile water. In one embodiment, the carrier is any injectable medium.

In one embodiment, the carrier is or comprises sterile, pyrogen-free water. In one embodiment, the carrier is or comprises 5% dextrose in water. In one embodiment, the carrier is or comprises ethanol. In one embodiment, the carrier is or comprises iodinated contrast.

The beta-radiation-emitting compositions may also produce some other radiation, as with radionuclides such as $^{3}$H, $^{14}$C, $^{32}$P, $^{59}$Fe, and $^{47}$Ca. However, the compositions typically use higher energy pure β-emitters such as $^{89}$Sr, $^{166}$Ho, $^{153}$Sm, $^{177}$Lu, $^{169}$Er and $^{90}$Y, and more typically compositions containing $^{90}$Y.

In various embodiments, the compositions contain $^{90}$Y radionuclide in glass particles or polymer particles, typically, in glass particles. The particles typically are microspheres. The particles typically have an average diameter of 1 to 100 μm. More typically, the particles have an average diameter or 10 to 50 μm, still more typically an average diameter of 15 to 35 μm, even more typically, an average diameter of 20 to 30 μm.

These particles are supplied in as a suitable suspension, and are typically and conveniently supplied in aqueous suspension (e.g., in sterile water or saline).

In various aspects, the treatment methods of the present disclosure deploy a catheter to the prostatic vasculature. For example, the catheter may be deployed to one or more left prostatic arteries, one or more right prostatic arteries, or both one or more left prostatic arteries and one or more right prostatic arteries. For example, a tumor may be located in one prostatic hemisphere or localized to a sub-zone of one prostatic hemisphere, and the catheter may be deployed to a particular branch of a prostatic artery that supplies a tumor. More typically, catheter may be deployed to a plurality of locations in the left and right prostatic arteries (both hemiglands) to maximize the volume of the prostate that is perfused.

In some embodiments, the β-radiation-emitting composition is delivered to a location in the prostatic arterial anatomy that is beyond potential nontarget vessels and proximal to potential intraprostatic branch points is to ensure thorough perfusion of the gland.

In some embodiments, steps are taken to identify prostatic arteries at risk of nontarget embolization, such as the vesical, rectal, and internal pudendal arteries (e.g., using preprocedural computed tomography angiography (CTA) or intraprocedural pelvic cone beam computed tomography (CBCT)), and embolization of these arteries (e.g., by coil embolization) can be performed prior to delivery of the β-radiation-emitting composition.

In some embodiments, the β-radiation-emitting composition is delivered to the anterior/lateral prostatic artery, which supplies the central gland tissue, whereas delivery to the posterior/lateral prostatic artery, which generally provides capsular supply, may be avoided in instances where the posterior/lateral prostatic artery has anastomoses to extraprostatic tissues, such as the rectum or penis. Delivery of the β-radiation-emitting composition to prostatic arteries having anastomoses to extraprostatic tissues may be avoided, for example, by coil embolization of such prostatic arteries as previously noted or by delivering the β-radiation-emitting composition to a location in the prostatic arterial anatomy that is distal to such prostatic arteries.

The catheter is typically a microcatheter. Examples of suitable microcatheters include the TruSelect™, a 2.0F microcatheter from Boston Scientific, and Maestro™, a 2.1 F microcatheter from Merit Medical Systems, Inc. Typically, the microcatheter is delivered over a guidewire. An example of a guidewire is the 0.014-inch Fathom™ microwire available from Boston Scientific. Typically, angiographic evaluation with contrast agents, e.g. iodinated contrast agents, are deployed, and the left and/or right prostatic arteries are identified and accessed in that manner.

One exemplary procedure may include the following steps: (a) establishing arterial access, (b) advancing the catheter into the abdominal aorta to the level of the iliac bifurcation, (c) performing intraprocedural pelvic cone beam computed tomography (CBCT) to map the origins of both prostatic arteries, and to confirm catheter placement and exclude nontarget embolization, (d) performing right internal iliac artery catheterization and angiography, (d) performing right prostatic artery catheterization and angiography, (e) embolizing right prostatic arteries, (f) performing left internal iliac artery catheterization and angiography, (g) performing left prostatic artery catheterization and angiography, and (h) embolizing left prostatic arteries.

In some embodiments, the target treatment volume will be determined. A medical professional may perform treatment planning at target prescribed absorbed dose to the whole gland of 60 Gy to 200 Gy, for example, ranging anywhere from 60 Gy to 75 Gy to 100 Gy to 125 Gy to 150 Gy to 175 Gy to 200 Gy, typically, ranging from 100 Gy to 175 Gy. This treatment dose is infused into the prostate through the microcatheter.

In some embodiments, the target treatment volume is understood as being the region perfused by the administration.

In some embodiments, a practitioner may use anatomical imaging (e.g., pre-treatment MRI) and/or intraprocedural cone beam computed tomography (CBCT) with contrast enhancement to determine the target treatment volume.

In some embodiments, the absorbed dose delivered in Gy can be calculated based upon target treatment volume using the MIRD Schema. In some embodiments, the desired absorbed dose in Gy can be calculated based upon target treatment volume using software similar to that of TheraSphere™ iDOC™ or Treatment Window Illustrator.

In some embodiments, the absorbed dose delivered may be calculated from perfused-tissue volumes (determined from cone-beam CT) with Simplicit$^{90}$Y™ (Mirada Medical, Denver, Colorado) according to TheraSphere™ labeling and the MIRD method. The treatment dosage (i.e. activity) may be selected based on the target prescribed absorbed dose.

In embodiments, an absorbed dose of 60 Gy to 200 Gy, for example, ranging anywhere from 60 Gy to 75 Gy to 100 Gy to 125 Gy to 150 Gy to 175 Gy to 200 Gy, typically, ranging from 100 Gy to 175 Gy, is delivered.

In some embodiments, the urethral vasculature of the patient is constricted while delivering the β-radiation-emitting composition. For example, the urethral vasculature may be constricted by cooling the urethra, by applying pressure using foley catheter, and/or by administration of one or more pharmacologic agents such as phenylephrine.

In particular embodiments, the urethral vasculature is constricted by cooling the patient's urethra, in which case the urethral vasculature may be constricted by conduction of heat from the urethra to a cooled catheter. In some embodiments, the cooled catheter is a Foley catheter and chilled fluid is introduced retrograde through the catheter into the patient's bladder. In some embodiments, a catheter may be employed in which liquid can be constantly circulated into and out of the catheter shaft.

After the microsphere infusion is completed, and closure and hemostasis are achieved, the subject may be transported to PET/CT or PET/MRI for scanning. PET/CT or PET/MRI will detect radioactive emissions from the administered particles. Confirmation of dose delivery with post-Y90 PET can be used to plan subsequent therapy including combination therapy with EBRT.

Potential post-operative pain may be managed with, for example, subcutaneous/IM injections of analgesic. The subject may be allowed to return home when awake and normothermic, following radiation safety survey. After the procedure and imaging, subjects may be discharged the same day.

In some embodiments, externally radiation therapy is applied to the prostate either before or after administration of the β-radiation-emitting composition.

EXAMPLES

The aim of this study was to establish a model of prostate artery embolization using TheraSphere™ Y90 in a canine benign prostatic hyperplasia (BPH) model. This study involved creating an established dog model of benign prostatic hyperplasia (BPH) and delivering radiation in the form of radioactive glass microspheres directly to the prostate through a catheter that is inserted into a groin blood vessel. A dose-escalation approach with unilateral Y90 prostate artery embolization was taken in order to determine a maximum tolerated dose in canine BPH models.

Methods:

Hormone-induced canine prostatic hyperplasia is a well-established model since BPH develops spontaneously in dogs. Briefly, 18 male castrated beagles were used on this study and underwent the required 3-month hormone administration procedure to induce prostatic hyperplasia. Further details can be found in Mouli S. K. et al. Yttrium-90 Radioembolization to the Prostate Gland: Proof of Concept in a Canine Model and Clinical Translation. *J. Vasc. Interv. Radiol.* 32(8): 1103-1112 (2021).

Of the 18 dogs, 2 initial dogs underwent embolization with nonradioactive/cold microspheres after hormone therapy for the purposes of microdosimetry analysis and demonstrating technical feasibility (0.5 and 1 GBq equivalent doses, respectively). Under fluoroscopic control, the mixture was slowly injected.

Following anesthesia induction, under the guidance of ultrasound, a 4-F vascular sheath (Radiofocus™; Terumo, Tokyo, Japan) was inserted into the right femoral artery using the Seldinger technique. Pelvic angiography was performed using a 4-F catheter (Cordis, Miami Lakes, Florida) to evaluate the iliac anatomy. Next, internal iliac arteriography was performed with an ipsilateral anterior oblique projection of 30°-40° to identify the prostatic arteries. Subsequently, selective angiography of the right or left prostatic artery was performed using either a coaxial 2.0-F or 2.1-F microcatheter (TruSelect™ from Boston Scientific; or Maestro™ from Merit Medical Systems, Inc.) and a 0.014-inch microwire (Fathom™; Boston Scientific).

Embolization was terminated when the entire vial of microspheres was delivered. Saline infusion was given on the contralateral side as a control. After transarterial prostatic embolization, the dogs were euthanized immediately for microsphere distribution analysis using a micro-CT scanner. The whole prostate was harvested, fixed in formalin, and scanned to get distribution confirmation of the microspheres.

Twelve animals assigned to three groups, (a) a low-dose group with the $^{90}$Y dose ranging from 60 to 70 Gy (n=4), (b) a medium-dose group with the $^{90}$Y dose ranging from 80 to 120 Gy (n=4), and (c) a high-dose group with the $^{90}$Y dose ranging from 150 to 200 Gy (n=4), and were treated with radioactive Y90 microspheres (TheraSphere™, Boston Scientific Corporation), again delivered to one prostatic-hemigland, with the contralateral side serving as the control. Four animals were divided into two groups for bilateral administration: a low-dose group with the $^{90}$Y dose of 50-60 Gy (n=2), (b) a medium-dose group with the $^{90}$Y dose ranging from 80 to 120 Gy (n=2). Prior to arterial access, a foley catheter was placed in the urethra, and cooled saline was administered through the catheter throughout the procedure. As above, femoral access was established percutaneously, a catheter was placed through the sheath into the right and left internal iliac arteries using fluoroscopy to obtain selective angiograms. The catheter was removed, heparin was given for systemic heparinization, and a delivery catheter was inserted through the sheath into the prostatic artery. Y90 TheraSphere™, in dose vial sizes of 0.53 GBq to 1.13 GBq (at calibration), were infused. A standard TheraSphere™ Administration Set, comprising a syringe, tubing, connection to the dose vial and connection to the microcatheter, all assembled with a TheraSphere™ Administration Accessory Kit, which includes beta radiation shielding, was used. A manual infusion using a 50 ml syringe was used to infuse cold saline through the system. 0.9% saline solution containing the TheraSphere™ was infused into the prostatic artery. During Y90 treatment, 11 of 12 dogs required coil embolization of extra-prostatic collateral vessels in order to prevent microsphere migration towards the bladder. Coil embolization procedure routinely performed to prevent non-target embolization during prostate artery embolization (PAE) for benign prostatic hyperplasia (BPH).

Once delivery of TheraSphere™ was complete, the catheter was withdrawn. The sheath was removed and hemostasis was achieved using pressure held on the femoral artery for at least 20 minutes. A commercial closure device involving a collagen plug to seal the artery was available in the event that hemostasis was not achieved.

In the immediate post-procedural period, monitoring was continued until the canine was sternal. Once sternal and with normal body temperature, the canine was returned to the animal facility and held in a separate cage with radioactive labels on the door (the canines were considered radioactive, so appropriate safety precautions were taken). At that point, the animal's groin was assessed for any complications (i.e. hematoma), and observed for any post-operative complications, including inappetence, hunching (a sign of pain), or inactivity. If any of these signs were present, veterinary staff would be notified for a consultation.

Cone beam CT imaging was used during the radioembolization procedure to evaluate prostatic vasculature. PET/MRI scan was taken within 1-day post-Y90 treatment to evaluate bead distribution in the prostatic vessels. PET-MRI provided post-delivery confirmation of absorbed dose distribution as well. The animals underwent periodic MRI imaging starting at baseline till tissue harvest. For imaging, an IV catheter was placed in a cephalic vein after sedation and a bag of 0.9% saline was attached. After induction with propofol, the dog was intubated and placed on gas anesthesia in a supine position. Chucks were placed below the animal and on top of the animal to prevent any contact with the MRI bed and coil attachment. A typical MRI examination consisted of axial T1 weighted turbo spin echo and T2 weighted spin echo images. Additional contrast-enhanced T1 weighted images were obtained using a gadolinium bolus administered via the IV catheter. Imaging time was less than 2 hours per dog. Radiologists measured the volume of the prostate across all scans to evaluate change in prostate size. Radiologists also noted any abnormalities or changes on imaging.

Euthanasia was performed by inducing the dogs with propofol 3-6 mg/kg IV, intubating and placing them on isoflurane anesthesia 1.5-3%. Euthasol (1 ml/5 kg or 87 mg/kg) IV was administered. The animals were scheduled for 40 days post administration recovery period, however due to scheduling concerns and associated COVID-19 pandemic, the recovery period ranged from 47 to 86 days post administration.

At necropsy, the prostate, rectum, bladder, urethra, penis, and neurovascular bundles were removed and processed for pathological assessment. Also during necropsy, the brain, heart, lungs, left and right kidneys, spleen, and liver were visually examined for any gross changes.

Blood samples were collected from six of the twelve animals on days 3, 20 and 40 post Y90 infusion and had a 375 IDEXX CBC (complete blood count) and 3638 IDEXX SDMA (symmetric dimethylarginine) Test analyses performed (IDEXX Laboratories, Inc., Westbrook, Maine, USA).

Results

Results from first two dogs (control procedure dogs) verified establishment of a BPH model and demonstrated technical success in delivering embolic spheres localized to one lobe of the prostate.

Prostatic hyperplasia was successful in all animals, based on the prostatic volume measurements from the pre-hormone and post-hormone treatment MRI scans.

Prostatic artery catheterization with radioembolization was deemed successful based on the PET/MRI sequences performed 1-day post-treatment. These scans were used for microsphere distribution confirmation.

Y90 radioembolization was successful in all animals, with delivery efficiency >95%, with a clear dose escalation achieved across the 12 treated animals. Administered doses for the sixteen dogs (three groups of four dogs; 2 bilateral dose groups of 2 dogs each) are shown in Table 1. No complications occurred during the procedure. Technical success was verified by qualitative agreement between intra-procedural cone beam computed tomography (CBCT) and subsequent post-treatment PET/MRI. Post Y90 PET suggested the absorbed dose distribution covered the central and peripheral zones.

TABLE 1

| Dose escalation groups | Perfused volume (mL) | Dosage vial size (GBq) | Absorbed dose (Gy) | BED (Gy) | EQD2 (Gy) |
|---|---|---|---|---|---|
| Group 1 (59-70 Gy) | 20.3 | 0.95 | 59.23 | 127.3 | 54.6 |
| | 13.2 | 0.55 | 66.85 | 153.6 | 65.8 |
| | 18.3 | 1.04 | 71.32 | 170.0 | 72.9 |
| | 24.7 | 1.07 | 71.53 | 170.8 | 73.2 |
| Group 2 (80-120 Gy) | 21.2 | 1.09 | 85.16 | 225.9 | 96.8 |
| | 15.0 | 1.08 | 89.02 | 242.8 | 104.1 |
| | 9.2 | 0.53 | 94.85 | 269.5 | 115.5 |
| | 12.8 | 0.92 | 114.43 | 368.6 | 157.9 |

TABLE 1-continued

| Dose escalation groups | Perfused volume (mL) | Dosage vial size (GBq) | Absorbed dose (Gy) | BED (Gy) | EQD2 (Gy) |
|---|---|---|---|---|---|
| Group 3 | 11.6 | 1.11 | 155.83 | 627.1 | 268.8 |
| (150-200 Gy) | 8.0 | 1.01 | 156.16 | 629.4 | 269.8 |
| | 10.9 | 1.13 | 167.96 | 715.5 | 306.6 |
| | 8.0 | 0.97 | 198.88 | 965.8 | 413.9 |
| Group 4 | 60.6 | 0.93 | 52.8 | 106.9 | 45.8 |
| (Bilateral 50- | | | | | |
| 60 Gy) | 55 | 0.97 | 58.8 | 125.9 | 54.0 |
| Group 5 | 31.2 | 0.97 | 102.2 | 304.9 | 130.7 |
| (Bilateral 80- | | | | | |
| 120 Gy) | 25.4 | 1.02 | 129.2 | 453.2 | 194.2 |

Table 1 lists a summary of perfused volumes and absorbed dose based on one-compartment medical internal radiation dose (MIRD) schema (see Gulec S A, Mesoloras G, Stabin M. Dosimetric techniques in 90Y-microsphere therapy of liver cancer: the MIRD equations for dose calculations. J Nucl Med 2006; 47:1209-1211). The mean absorbed dose per animal ranged from 52.8 Gy-198.8 Gy and the EQD2 ranged from 45.8 Gy-413.9 Gy.

Throughout the clinical follow-up, across all dose groups, no adverse events were noted according to CTCAE v5.0 genitourinary and colorectal toxicities. (The National Cancer Institute (NCI) of the National Institutes of Health (NIH) has published standardized definitions for adverse events (AEs), known as the Common Terminology Criteria for Adverse Events (CTCAE), to describe the severity of organ toxicity for patients receiving cancer therapy, the most recent of which is CTCAE (version 5.0); a comprehensive listing of the v5.0 CTCAE is available from the National Cancer Institute (NCI) on the Cancer Therapy Evaluation Program (CTEP) website.) There were no significant alterations in serum chemistries across all dose groups throughout the duration of the study. There were no issues with urinary retention, incontinence, hematuria, diarrhea, perianal inflammation or necrosis, or rectal bleeding.

PET-MRI imaging conducted 1 day post administration demonstrated localization to, and good coverage of, only the treated hemigland of the prostate.

MRI Imaging showed a significant dose-dependent decrease in treated hemigland size at 40 days (25-60%, $p<0.001$). No extra-prostatic radiographic changes were observed.

MRI demonstrated significant volume changes following Y90 radioembolization across all dose groups that progressed over time (see Table 2). The volume of the treated hemigland significantly decreased 3 days following treatment by 12.0+/−19.0% ($P<0.001$), and continued to decrease throughout the follow-up period compared to baseline: 20 day: 32+/−23% ($p<0.001$); and 40 day: 51+/−26% ($p<0.001$). There was a negative correlation between volume change within the treated hemigland with dose escalation ($R=-0.4$; $P<0.001$), with the lowest dose group demonstrating an average decrease in size of 25% vs. 60% in the highest dose group ($P<0.001$). Although the volume of the contralateral side demonstrated volume reduction (18+/−7%; $p<0.05$), it did not significantly change across the dose groups ($P>0.05$).

TABLE 2

| Dose escalation groups | Absorbed dose (Gy) | Volume of Y90 treated half of the prostate (cc): Pre-Y90 admin | 3-Day post Y90 | 20-day post Y90 | 40-day post Y90 |
|---|---|---|---|---|---|
| Group 1 | 59.23 | 20.3 | 19.8 | 11.3 | 4.0 |
| (59-70 | 66.85 | 13.2 | 8.7 | 5.4 | 3.3 |
| Gy) | 71.32 | 18.3 | 15.3 | 12.0 | 6.2 |
| | 71.53 | 24.7 | 24.6 | 23.6 | 20.0 |
| Group 2 | 85.16 | 21.2 | 16.4 | 18.9 | 17.4 |
| (80-120 | 89.02 | 15.0 | 13.6 | 13.3 | 11.2 |
| Gy) | 94.85 | 9.2 | 11.4 | 6.0 | 3.3 |
| | 114.43 | 12.8 | 11.4 | 5.3 | 3.3 |
| Group 3 | 155.83 | 11.6 | 11.3 | 10.5 | 9.6 |
| (150-200 | 156.16 | 8.0 | 7.0 | 3.6 | 2.1 |
| Gy) | 167.96 | 10.9 | 10.8 | 10.8 | 7.9 |
| | 198.88 | 8.0 | 3.6 | 2.9 | 2.5 |

Necropsy demonstrated no gross rectal, urethral, penile or bladder changes. Histology revealed RE-induced changes in treated prostatic tissues of the highest dose group, with gland atrophy and focal necrosis. No extra-prostatic RE-related histologic findings were observed. Pathologic changes attributable to radiation exposure were noted in a dose-dependent fashion, most pronounced in the high-dose dogs, and consisted of decreased numbers of prostatic glands, degeneration and inflammation of prostatic glands, atrophy of the prostatic glands, and glandular epithelial metaplasia within the treated hemigland. While minor pathologic changes were observed in the control hemigland (due to microscopic cross-collaterals), the majority of the control hemigland was histologically unremarkable. No radiation induced pathologic changes were noted in extra-prostatic tissues including the bladder, urethra, penis, NVBs, or rectum. A few scattered microspheres ($n<10$) were noted in extra-prostatic tissues, and only in the highest dose group. The microsphere number was significantly less than those seen in either the treated hemigland or untreated hemigland ($P<0.0001$). Despite the presence of isolated microspheres in tissues such as the bladder ($n=1$), rectum ($n=1$), or NVB ($n=1$), there was no evidence of tissue damage with preservation of all surrounding structures and histologic architecture. Further results in addition to those described hereinabove can be found in Mouli S. K. et al. *J. Vasc. Interv. Radiol.* 32(8): 1103-1112 (2021).

The invention claimed is:

1. A method of treating a patient in need of therapy for prostate cancer comprising delivering a β-radiation-emitting composition through a catheter into the arterial prostatic vasculature, wherein the β-radiation-emitting composition comprises β-radiation-emitting microspheres that have mean diameter of 10 to 50 μm, wherein the β-radiation-emitting-microspheres comprise insoluble glass microspheres having yttrium-90 ($^{90}Y$) as a constituent of the glass, wherein the microspheres have a specific activity per microsphere of 50 to 2,000 Bq when administered, wherein from 5,000 to 30,000 microspheres per mL of prostate tissue are delivered, and wherein an absorbed dose of 60 Gy to 200 Gy is delivered from the β-radiation-emitting composition to the whole prostate gland.

2. The method of claim 1, further comprising constricting the urethral vasculature of the patient while delivering the β-radiation-emitting composition.

3. The method of claim 1, wherein the β-radiation-emitting composition comprises a suspension of the β-radiation-emitting microspheres in an aqueous liquid.

4. The method of claim 1, wherein each milligram of glass contains between 22,000 and 73,000 microspheres.

5. The method of claim 1, wherein the β-radiation-emitting particles have a specific activity when administered ranging from 0.0002 to 0.05 GBq/mg.

6. The method of claim 1, wherein the β-radiation-emitting composition is used in combination with externally applied radiation therapy.

7. The method of claim 1, further comprising embolizing the prostatic vasculature to isolate the prostatic arteries.

8. The method of claim 1, wherein dose delivery is confirmed with post-Y90 PET and used to plan subsequent therapy.

9. The method of claim 1, wherein the glass microspheres are derived from a mixture of 35-45% $Y_2O_3$, 15-25% $Al_2O_3$ and 35-45% $SiO_2$.

10. The method of claim 1, further comprising embolizing the prostatic vasculature to isolate the prostatic arteries.

11. A method of treating a patient in need of therapy for prostate cancer comprising delivering a β-radiation-emitting composition that comprises β-radiation-emitting microspheres through a catheter into the arterial vasculature of the prostate, wherein the urethral vasculature of the patient is constricted while delivering the β-radiation-emitting composition, wherein the β-radiation-emitting composition comprises β-radiation-emitting microspheres that have mean diameter of 10 to 50 μm, wherein the β-radiation-emitting-microspheres comprise insoluble glass microspheres having yttrium-90 ($^{90}Y$) as a constituent of the glass, wherein the microspheres have a specific activity per microsphere of 50 to 2,000 Bq when administered, wherein from 5,000 to 30,000 microspheres per mL of prostate tissue are delivered, and wherein an absorbed dose of 60 Gy to 200 Gy is delivered from the β-radiation-emitting composition to the whole prostate gland.

12. The method of claim 11, wherein each milligram of glass contains between 22,000 and 73,000 microspheres.

13. A method of treating a patient in need of therapy for prostate cancer comprising embolizing the prostatic vasculature of the patient to isolate the prostatic arteries; and delivering a β-radiation-emitting composition that comprises β-radiation-emitting microspheres through a catheter into the arterial vasculature of the prostate, wherein the β-radiation-emitting composition comprises β-radiation-emitting microspheres that have mean diameter of 10 to 50 μm, wherein the β-radiation-emitting-microspheres comprise insoluble glass microspheres having yttrium-90 ($^{90}Y$) as a constituent of the glass, wherein the microspheres have a specific activity per microsphere of 50 to 2,000 Bq when administered, wherein from 5,000 to 30,000 microspheres per mL of prostate tissue are delivered, and wherein an absorbed dose of 60 Gy to 200 Gy is delivered from the β-radiation-emitting composition to the whole prostate gland.

14. The method of claim 13, wherein each milligram of glass contains between 22,000 and 73,000 microspheres.

* * * * *